(12) United States Patent
Potter

(10) Patent No.: US 8,864,807 B2
(45) Date of Patent: Oct. 21, 2014

(54) THERMAL REGULATION BLANKET AND METHOD OF USE THEREOF

(75) Inventor: Charles F. Potter, Mequon, WI (US)

(73) Assignee: Medical Thermodynamics LLC, Neenah, WI (US)

( * ) Notice: Subject to any disclaimer, the term of this patent is extended or adjusted under 35 U.S.C. 154(b) by 552 days.

(21) Appl. No.: 13/046,316

(22) Filed: Mar. 11, 2011

(65) Prior Publication Data

US 2011/0224760 A1   Sep. 15, 2011

Related U.S. Application Data

(60) Provisional application No. 61/313,384, filed on Mar. 12, 2010.

(51) Int. Cl.
| | | |
|---|---|---|
| *A61F 7/03* | (2006.01) | |
| *A61F 7/00* | (2006.01) | |
| *A61F 7/02* | (2006.01) | |

(52) U.S. Cl.
CPC ................ *A61F 7/0097* (2013.01); *A61F 7/03* (2013.01); *A61F 2007/0001* (2013.01); *A61F 2007/0276* (2013.01); *A61F 2007/0247* (2013.01)
USPC ......................................... 607/114; 607/108

(58) Field of Classification Search
CPC . A61F 7/0097; A61F 7/03; A61F 2007/0001; A61F 2007/0022; A61F 2007/0276
USPC .................................................. 607/108, 114
See application file for complete search history.

(56) References Cited

U.S. PATENT DOCUMENTS

| | | | | |
|---|---|---|---|---|
| 2,403,676 A | | 7/1946 | Modlinski | |
| 3,019,952 A | | 2/1962 | Brewster | |
| 3,429,315 A | * | 2/1969 | McDonald | 607/112 |
| 3,506,013 A | * | 4/1970 | Zdenek | 607/108 |
| 3,714,947 A | * | 2/1973 | Hardy | 607/104 |
| 3,822,705 A | * | 7/1974 | Pilotte | 607/108 |

(Continued)

OTHER PUBLICATIONS

Polderman, K.H.; Abstract of Application of therapeutic hypothermia in the intensive care unit. Opportunities and pitfalls of a promising treatment modality—Part 2: Practical aspects and side effect; Intensive Care Medicine, vol. 30, No. 12, Dec. 30, 2004.

(Continued)

*Primary Examiner* — Linda Dvorak
*Assistant Examiner* — Kaitlyn Smith
(74) *Attorney, Agent, or Firm* — Rathe Lindenbaum LLP

(57) ABSTRACT

A thermal regulation blanket includes a plurality of cells with a first reagent. A plurality of pouches with a second reagent are disposed within the plurality of cells. A plurality of dividers are disposed between each of the plurality of cells. A thermally conductive layer is disposed over the cells and the plurality of dividers. When the first reagent and the second reagent mix, a thermal reaction occurs which modifies a temperature of the thermally conductive layer. A method of providing thermal therapy to a patient includes positioning the patient on a thermal regulation blanket, an abdomen of the patient is engaged with at least one abdominal blanket of the thermal regulation blanket. At least one cell of the thermal regulation blanket is activated to begin providing thermal therapy to the patient. A temperature of the thermal regulation blanket is monitored with a temperature sensor. At least one additional cell is activated to adjust the temperature of the thermal regulation blanket.

14 Claims, 7 Drawing Sheets

(56) References Cited

U.S. PATENT DOCUMENTS

| | | | |
|---|---|---|---|
| 3,865,117 A * | 2/1975 | Perry, III | 607/114 |
| 3,893,834 A | 7/1975 | Armstrong | |
| 4,081,256 A | 3/1978 | Donnelly | |
| 4,527,566 A | 7/1985 | Abare | |
| 4,556,055 A | 12/1985 | Bonner, Jr. | |
| 4,592,358 A * | 6/1986 | Westplate | 607/112 |
| 4,745,922 A | 5/1988 | Taylor | |
| 4,981,135 A * | 1/1991 | Hardy | 607/108 |
| 4,985,934 A | 1/1991 | Perry | |
| 5,020,711 A * | 6/1991 | Kelley | 224/222 |
| 5,146,625 A | 9/1992 | Steele et al. | |
| 5,302,806 A | 4/1994 | Simmons et al. | |
| 5,584,086 A * | 12/1996 | VanWinkle et al. | 5/644 |
| 5,605,144 A | 2/1997 | Simmons et al. | |
| 5,737,774 A * | 4/1998 | Petty-Saphon et al. | 2/69 |
| 5,823,984 A | 10/1998 | Silverberg | |
| 5,826,273 A | 10/1998 | Eckes | |
| 5,840,080 A | 11/1998 | Der Ovanesian | |
| 5,891,187 A | 4/1999 | Winthrop et al. | |
| 5,897,582 A * | 4/1999 | Agnatovech et al. | 607/109 |
| 6,030,412 A | 2/2000 | Klatz et al. | |
| 6,113,626 A | 9/2000 | Clifton et al. | |
| 6,523,354 B1 | 2/2003 | Tolbert | |
| 6,598,235 B2 | 7/2003 | Bulla | |
| 6,699,271 B2 | 3/2004 | Clayton | |
| 7,087,075 B2 * | 8/2006 | Briscoe et al. | 607/104 |
| D573,777 S | 7/2008 | Rogers | |
| D599,529 S | 9/2009 | Simpson | |
| 7,766,950 B2 * | 8/2010 | Castellani et al. | 607/108 |
| 7,846,118 B2 | 12/2010 | Sandhu | |
| 7,950,385 B2 * | 5/2011 | Ohnishi et al. | 126/263.01 |
| RE43,033 E | 12/2011 | James et al. | |
| 8,361,133 B2 * | 1/2013 | Cushman et al. | 607/108 |
| 2001/0027334 A1 | 10/2001 | White | |
| 2003/0109911 A1 * | 6/2003 | Lachenbruch et al. | 607/112 |
| 2004/0064170 A1 * | 4/2004 | Radons et al. | 607/104 |
| 2004/0064171 A1 * | 4/2004 | Briscoe et al. | 607/104 |
| 2005/0044602 A1 * | 3/2005 | Leach, II | 2/69 |
| 2006/0155351 A1 * | 7/2006 | Matson | 607/114 |
| 2007/0150033 A1 | 6/2007 | Johnson et al. | |
| 2007/0185370 A1 * | 8/2007 | Eyck | 600/22 |
| 2007/0284356 A1 * | 12/2007 | Findlay | 219/212 |
| 2009/0198311 A1 | 8/2009 | Johnson et al. | |
| 2009/0299442 A1 * | 12/2009 | Vergona et al. | 607/114 |
| 2010/0089896 A1 * | 4/2010 | Bart | 219/211 |
| 2010/0280581 A1 * | 11/2010 | Cushman et al. | 607/112 |
| 2011/0224760 A1 | 9/2011 | Potter | |

OTHER PUBLICATIONS

Pretre, Rene et al. Deep Hypothermic Circulatory Arrest; Cardiac Surgery in the Adult; McGraw-Hill, 2003; pp. 1-21.

Polderman, Kees H. et al. Therapeutic hypothermia and controlled normothermia in the intensive care unit: Practical considerations, side effects, and cooling methods. Critical Care Medicine, vol. 37, No. 3, 2009, pp. 1101-1117.

* cited by examiner

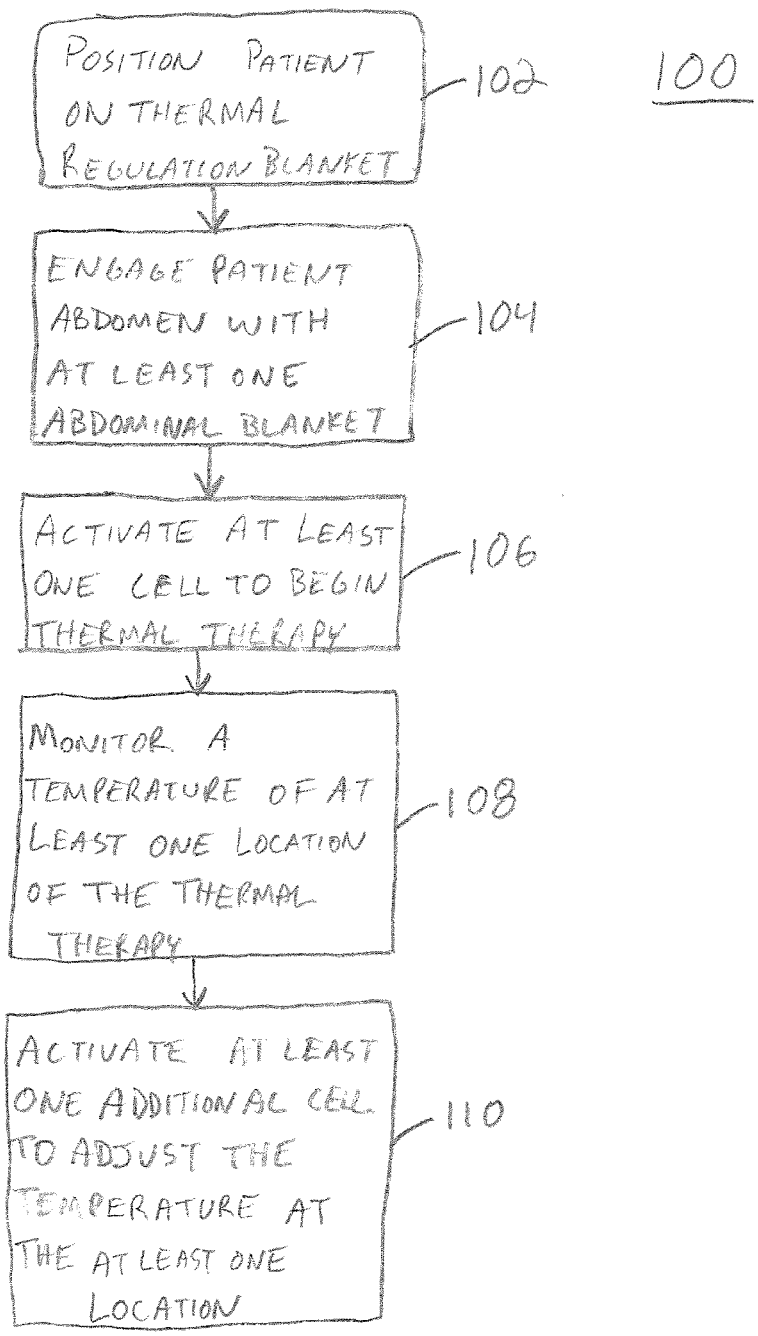

THERMAL REGULATION BLANKET AND METHOD OF USE THEREOF

CROSS REFERENCE TO RELATED APPLICATION

This application relates to and claims priority from U.S. Provisional Application Ser. No. 61/313,384 filed on Mar. 12, 2010.

FIELD OF THE DISCLOSURE

The present disclosure is related to the field of thermal therapy. More specifically, the present disclosure is related to a thermal regulation blanket and a method of providing thermal therapy to a patient with a thermal regulation blanket.

BACKGROUND

Lowering a temperature of a mammal, such as a human, (hypothermia) to 31-34 degrees C. can be beneficial during times of critical care. Examples of these situations include, but are not limited to, myocardial infarction and cardiac arrest, stroke, and infantile asphyxia. Hypothermic outcomes are improved when therapy is initiated as soon as possible after the initial onset of the affliction in order to mitigate or prevent the affliction's damaging effects. Current hypothermic therapy technology is hospital based as available systems require a large refrigeration unit to circulate a cooling fluid in specialized mats covering the patient while the unit closely regulates the patient's temperature. Precise thermal regulation is required in these systems to promote effective cooling while also limiting its side effects such as frost bite/tissue damage, electrolyte changes, hypotension, and infection.

There is often an inherent delay in starting hypothermic therapy from the time of symptom presentation to cooling induction as the patient must be transported to the hospital, the refrigeration unit needs to be set up, and the cooling mats placed. As noted above, delay in initiating therapy decreases effectiveness, and currently available systems for the initiation of hypothermia outside of a hospital setting include the use of cold saline IV infusion or ice packs placed on the patient. Both of these currently available procedures lack temperature control to provide regulation of the thermal therapy, are difficult to initiate in the field (need for an IV, ambulance refrigerator, etc.), and are difficult to provide consistent therapy across patients.

BRIEF DISCLOSURE

An embodiment of a thermal regulation blanket includes a plurality of cells. Each of the cells of the plurality includes a first reagent. A plurality of pouches are disposed within respective cells of the plurality of cells. Each of the pouches include a second reagent. A plurality of dividers are disposed between each of the plurality of cells. A thermally conductive layer is disposed over the plurality of cells and the plurality of dividers. The rupture of a pouch of the plurality of pouches causes the second reagent to mix with the first reagent of the respective cell. When the first reagent and the second reagent mix, a thermal reaction occurs which modifies a temperature of the thermally conductive layer.

A thermal regulation blanket includes a body blanket constructed of a first plurality of cells. The first plurality of cells are separated by a plurality of dividers. Each of the cells of the first plurality of cells includes a first reagent. A first plurality of pouches are each disposed within a respective cell of the first plurality of cells. Each pouch of the first plurality of pouches includes a second reagent. A first thermally conductive layer is disposed over the first plurality of cells and the plurality of dividers. The thermally conductive layer creates a thermal interface between the patient and the first plurality of cells. The thermal regulation blanket includes a body blanket and at least one abdominal blanket. The abdominal blanket is constructed of a second plurality of cells that each include the first reagent. A second plurality of pouches each include the second reagent. Each of the second plurality of pouches are disposed within a respective cell of the second plurality of cells. A second thermally conductive layer is disposed over the second plurality of cells. The at least one abdominal blanket is dimensioned to cover a substantially smaller portion of the patient's torso than the body blanket. The at least one abdominal blanket aligns with a portion of the patient's torso below the shoulders. Rupture of any pouch of the first or second plurality of pouches causes the second reagent to mix to with the first reagent within the respective cell. When the first reagent and the second reagent mix, a thermal reaction occurs that modifies the temperature of a respective thermally conductive layer.

A method of providing thermal therapy to a patient includes positioning the patient on a thermal regulation blanket. The thermal regulation blanket includes a plurality of cells filed with a first reagent, a pouch disposed within each of the plurality of cells, each pouch filled with a second reagent. At least one abdominal blanket of the thermal regulation blanket engages an abdomen of the patient. The at least one abdominal blanket includes at least one cell of the plurality of cells. At least one cell of the plurality of cells is activated by mixing the first reagent and the second reagent in the at least one cell to begin providing thermal therapy to the patient. A temperature of at least one location of the thermal regulation blanket is monitored with a temperature sensor. At least one additional cell is activated to adjust the temperature of the at least one location.

BRIEF DESCRIPTION OF THE DRAWINGS

FIG. 7 is a flow chart that depicts an embodiment of a method of providing thermal therapy to a patient.

DETAILED DESCRIPTION

Figure 1:
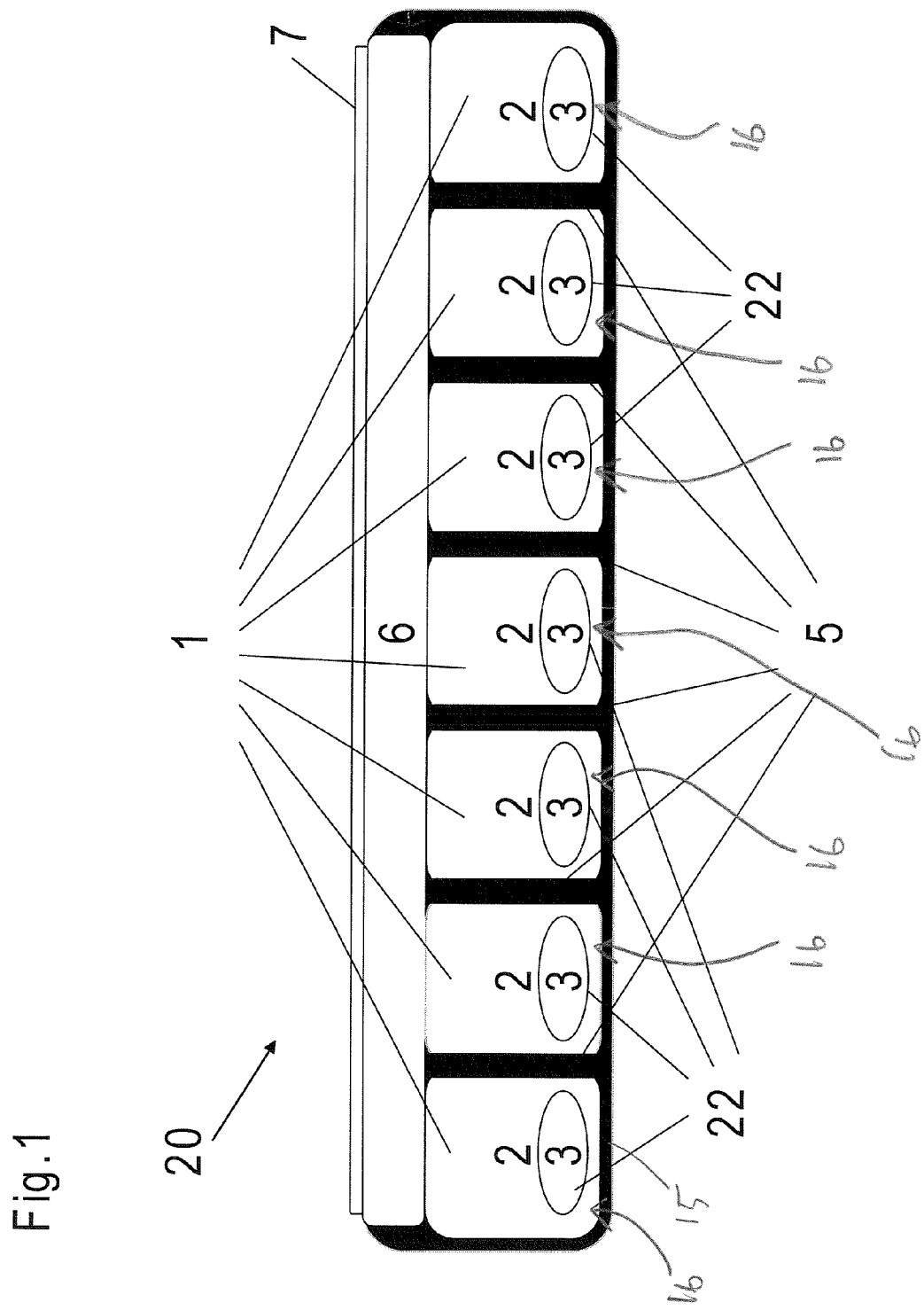
FIG. 1 is a cross-sectional view through an embodiment of a thermal regulation blanket.

FIG. 1 is a cross-sectional view through an embodiment of a thermal regulation blanket 20. The present disclosure will focus on the functionality of an embodiment of a thermal regulation blanket 20 that provides cooling therapy. However, it has been recognized by the inventor that embodiments of the thermal regulation blanket that provide heating therapy can also comprise the same disclosed features with minimal modifications as disclosed in further detail herein.

The thermal regulation blanket 20 includes several cells 1. In an embodiment, each of the cells 1 measure several inches in circumference. As will be disclosed in further detail herein, each of the cells 1 are generally of an elongated and tubular shape, of which FIG. 1 depicts a cross-section. In an embodiment, the cells 1 are constructed of plastic; however, this is not intended to be limiting and a person of ordinary skill in the art would recognize any of a variety of suitable materials for the cells, including, but not limited to, polyethylene terephthalate, polyethylene, polyvinyl chloride, vinyl, polypropylene, polystyrene, resins, or materials specifically designed for contact with a patient.

Each of the cells 1 are filled with a first reagent 2. Disposed within each of the cells 1 is a pouch 22. The pouch 22 may be of a similar construction to that of the cell 1; however, in some embodiments disclosed in further detail herein, the pouch 22 is rupturable, and therefore designed to break under conditions upon which the cell 1 does not. The pouch 22 is filled with a second reagent 3. In one embodiment, the first reagent 2 is water (H2O) and the second reagent 3 is Ammonium Nitrate. As disclosed in further detail herein, the first reagent 2 and second reagent 3 are both selected with the consideration that a thermal reaction occurs upon the mixing of the two reagents. In the embodiment described above, the thermal reaction is an endothermic reaction that decreases the temperature of the cell 1. It is understood that by modifying the specific substances selected as first reagent 2 and second reagent 3, that alternative endothermic reactions or an exothermic reaction would occur upon the mixing of the two reagents.

In an alternative embodiment, the first reagent 2 and second reagent 3 may be selected from combinations of chemicals that when combined provide an exothermic reaction. Such combinations of chemicals may include sodium acetate, H2O, and thickeners that provide an exothermic reaction when combined. Some such exothermic reactions can be activated by the manipulation of a metal disk (not depicted). This is as described in U.S. Pat. No. 5,058,563, which is herein incorporated by reference in its entirety.

As will be described in further detail herein, the specific concentrations of the first reagent 2 and the second reagent 3 within each of the cells 1 need not be identical. An exemplary ratio of H2O to Ammonium Nitrate in the disclosed embodiment is 3/4-2; however this ratio may be strengthened or weakened in an effort to produce stronger or weaker endothermic reactions in each of the cells. Other compounds such as organic/inorganic salts or crystalline polymers may be added to attenuate, amplify, augment, or prolong the reaction to improve the efficiency of the blanket, or to impart divergent thermal reaction properties to different cells 1 of the blanket 20.

A thermally conductive layer 6 is located above and across the cells 1. In an embodiment, the thermally conductive layer 6 is composed of a gel of glycerol or another appropriate substance as recognized by one of ordinary skill in the art. In an embodiment, the thermally conductive layer 6 includes a flexible plastic compartment coupled to the plurality of cells, and the conductive gel is contained within the flexible plastic compartment. In an alternative embodiment, the thermally conductive layer 6 is a solid material structure, such a foam or Styrofoam. The thermally conductive layer 6 increases surface area contact between the patient (not depicted) and the blanket 20 while evenly distributing the cooling potential of the activated cells 1 of the blanket 20. The distribution of the cooling potential of the activated cells also helps to protect the patient from contact with any localized temperature extremes. To these ends, as can be seen from the exemplary materials identified for the thermally conductive layer 6, the specific material of the thermally conductive layer 6 can be selected to balance considerations of transferring the cooling (or heating) potential from the activated cells 1 to the patient, as well as protecting the patient from excessive direct exposure to the thermal (hot or cold) source of the activated cells 1. This results in embodiments of the thermally conductive layer 6 that vary in ability to conduct thermal energy.

The blanket 20 further includes a plurality of dividers 5 disposed between each of the cells 1. The dividers 5 are constructed of a rigid or semi-rigid material such that the dividers 5 provide support to the blanket 20. This structural support provided by the plurality of dividers 5 maintain the shape of the blanket 20 under the weight of a patient positioned on top of the blanket 20, such as on the thermally conductive layer 6. Therefore the dividers 5 prevent the premature rupture of any of the pouches 22 when a patient is positioned on the blanket 20. The dividers further maintain each of the cells 1 in an open configuration, such that the weight of a patient positioned on top of the blanket 20 does not pinch, kink, or otherwise impede the mixture and reaction of the first reagent 2 and the second reagent 3 once the reagents have been combined inside the cell 1. In an embodiment, the dividers 5 also allow the weight of the patient to push gas produced by the chemical reaction to the edges of the blanket, thus removing a possible insulator against effective cooling. In an embodiment, the dividers are further connected to each other by a divider base 15. The divider base 15 and each of the plurality of dividers 5 form a plurality of structural channels 16 within which each of the cells 1 are disposed. In one embodiment, the divider 5 and the divider base 15 are constructed of an insulative material, exemplarily Styrofoam. This insulative material provides the additional benefit of insulating each of the cells 1, such that the cooling potential created by each of the activated cells is directed towards the thermally conductive layer 6 and not lost in the direction away from the patient, which may exemplarily be the ground.

Figure 3:
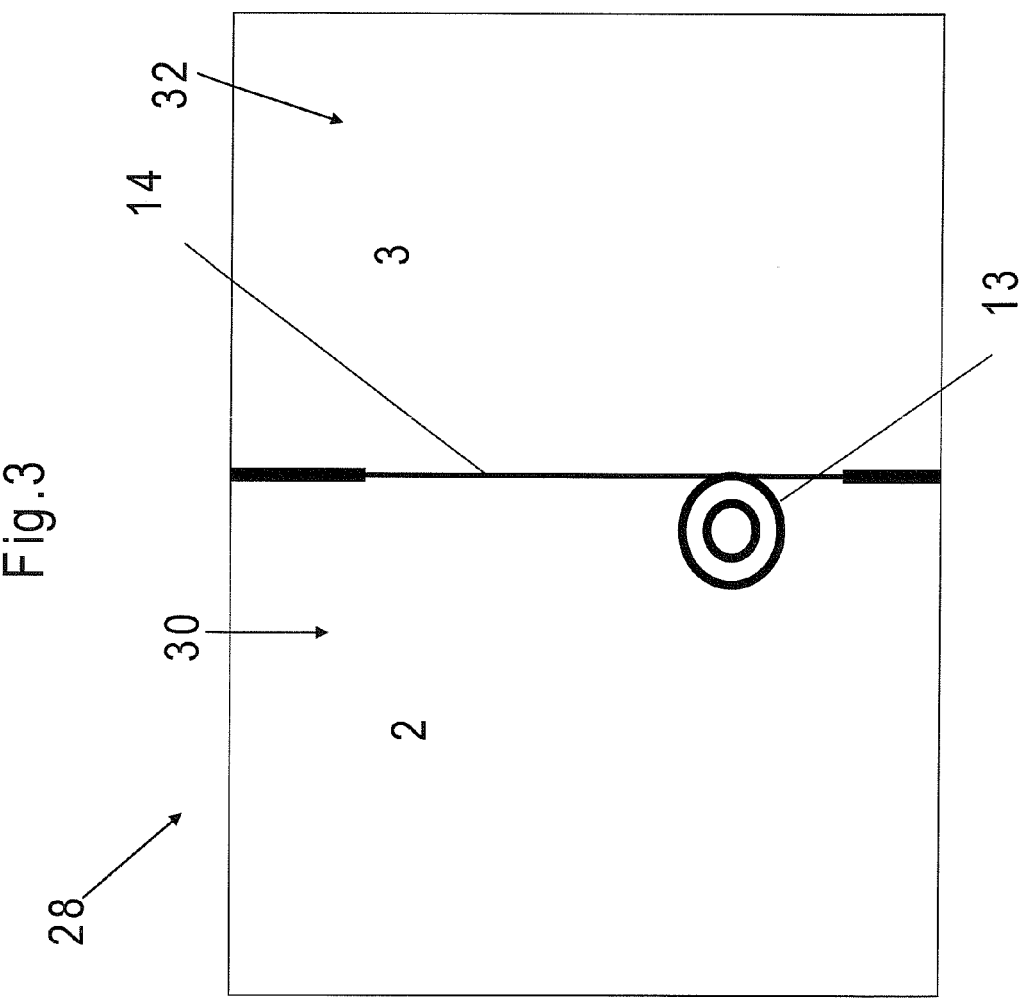
FIG. 3 is a cross-sectional view of through an alternative embodiment of a cell.

FIG. 3 depicts a cross-sectional view of an alternative embodiment of a cell 28 that may be used in embodiments of the blanket 20 as disclosed herein. The cell 28 includes a plastic partition 14 between opposing halves 30,32 of the cell 28. The first reagent 2, which may be H2O, is disposed within the first half 30 and the second reagent 3, which may be Ammonium Nitrate, is disposed within the second half 32. It is understood that while opposing halves 30,32 are described herein as halves, the actual volumetric proportions of the two spaces can vary with the volumes of the respective reagents. Furthermore, while described as a half, the second half 32 may be identical in structure and function as the pouch 22 (FIG. 1). The partition 14 separates the first reagent 2 and the second reagent 3 from mixing until manipulation by a clinician. In one embodiment, the partition 14 ruptures upon the application of a predetermined amount of pressure, likely less than an amount of pressure required to rupture the cell 28. In a still further embodiment, an attachment 13, which may be a string, spring, rubber band, or the like, is connected to the partition 14. Manipulating the attachment 13, such as by pulling, cutting, releasing, or some other form of actuation removes or opens the partition, thus allowing the first reagent 2 and the second reagent 3 to mix and an endothermic reaction to proceed throughout the length of the cell 28.

Figure 2:
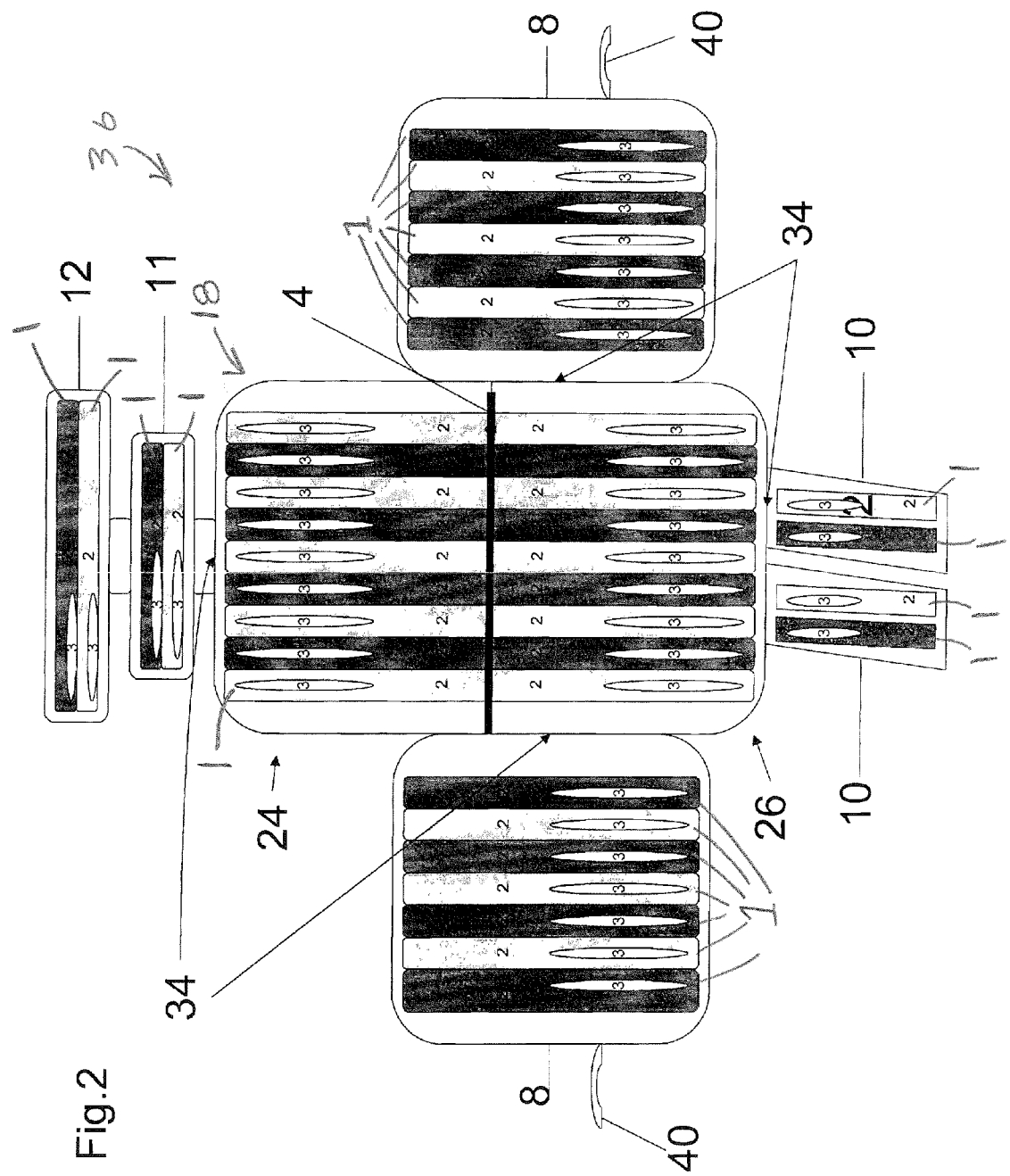
FIG. 2 depicts an embodiment of a thermal regulation blanket.
Figure 6:
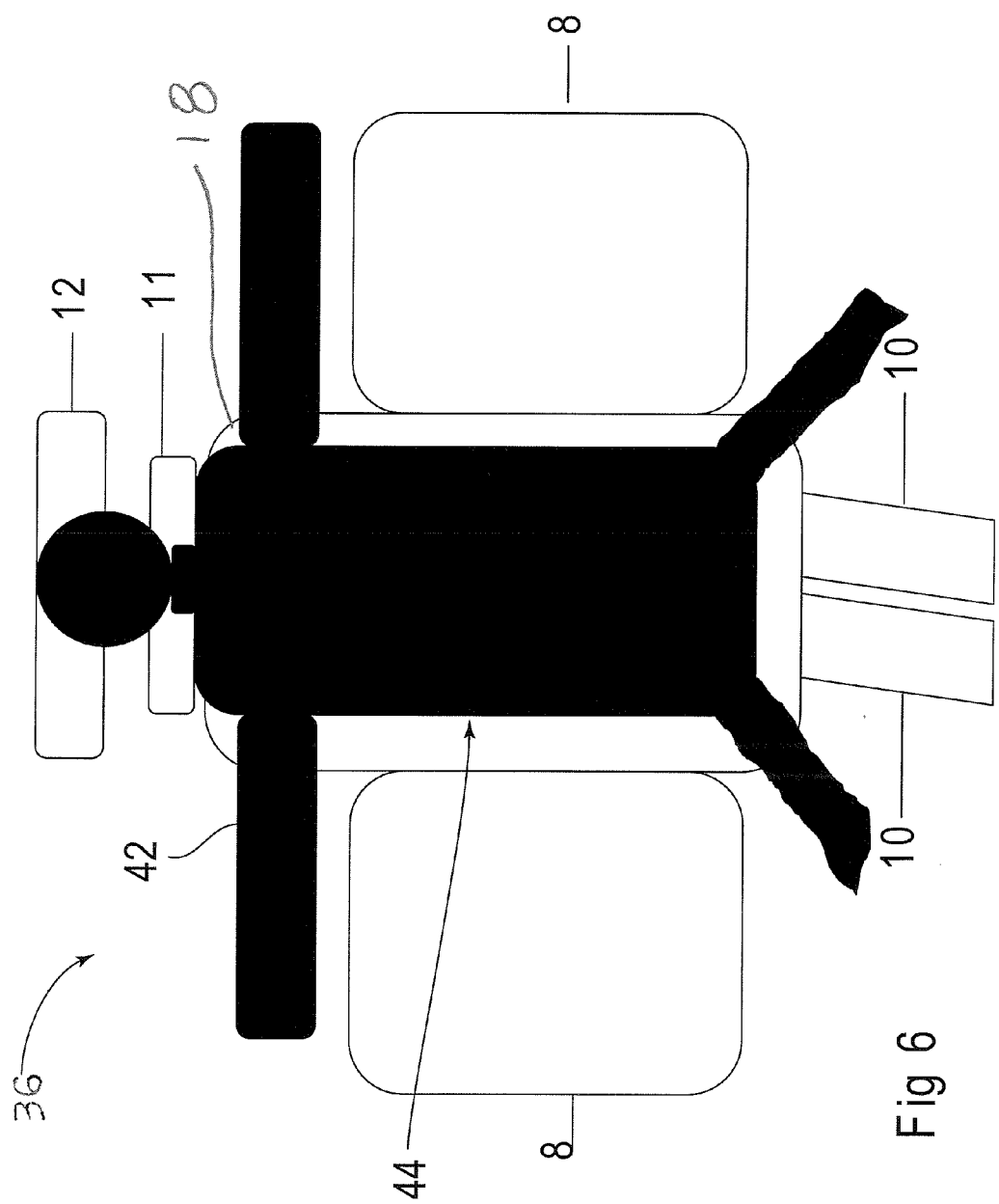
FIG. 6 depicts a patient oriented on an embodiment of a cooling blanket.

Referring now to FIGS. 2 and 6, an alternative embodiment of the thermal regulation blanket 36 is disclosed. The thermal regulation blanket 36 includes a plurality of elongated cells 1 that are formed into various functional regions or components of the thermal regulation blanket 36. In the embodiment depicted, the thermal regulation blanket 36 includes a body blanket 18, an abdominal blanket 8, a groin wrap 10, a neck wrap 11, and a head wrap 12. While not depicted, it is understood that embodiments of the thermal regulation blanket 36 may also include the dividers and thermally conductive layer depicted in FIG. 1, while these components are not depicted in FIG. 2 in order to simplify the drawing to focus on other details.

The thermal regulation blanket 36 provides a patient cooling surface area through direct contact between the patient 42 and the blanket 36. Each of the functional regions of the blanket 36 identified above are designed to target cooling of the patient 42 at different anatomical locations, such as the back, buttocks, abdomen, groin, legs, arms, neck and head of the patient 42. These anatomical locations are targeted in part, as described in further detail herein, due to the presence of major vasculature in the body the targeted exposure of the major vasculature to the thermal therapy helps to promote quick and effective introduction of thermal therapy to the patient 42.

The body blanket 18 is dimensioned to fit the torso and buttocks of an adult patient. In an embodiment, this results in a body blanket 18 that is between 3-5 feet in length and between 2-3 feet in width. However, it is understood that the above dimensions of the blanket 36 are merely exemplary and are not intending to be limiting on the size and construction of embodiments of the blanket as disclosed herein. Cells 1 are elongated in one dimension to run the length of the body blanket 18. In the embodiment depicted, the body blanket 18 is divided in half by a middle seam 4. Such a seam allows improved flexibility to allow folding for improved storage of the blanket 36. Thus it is understood that the cells 1 can be of any length along the body blanket. Exemplarily, the middle seam 4 divides the body blanket 18 into an upper portion 24 and a lower portion 26.

Auxiliary blankets and wraps (8,10, 11,12) are releasably attached to the body blanket 18. The auxiliary blankets and wraps can be releasably attached by with perforated edges 34 such that the auxiliary blankets and wraps can be easily removed to manipulate a blanket 36 dimensioned for an adult into a device suitable for cooling a child or infant. Alternatively, the auxiliary blankets and wraps can be repeatably attached to the body blanket 18, such as by zippers, buttons, or hook-and-loop fasteners.

As depicted in FIG. 6, the patient 42 is positioned on top of the blanket 36 with his back and buttocks against the body blanket 18. The patient's abdomen is cooled by one or more abdominal blankets 8 which may have merely exemplary dimensions of eighteen inches by eighteen inches. It is understood that embodiments of the abdominal blanket 8 are dimensioned to facilitate and promote the functions of the abdominal blanket as disclosed herein. The abdominal blanket 8 may be distinguished from the body blanket 18 in that the abdominal blanket 8 lacks the dividers (not depicted) found between the cells 1 in embodiments of the blanket 36. The lack of the dividers in embodiments of the abdominal blankets 8 increases the flexibility of the abdominal blankets 8 such that they may be secured tightly over the abdomen of the patient 42. The abdominal blanket 8 may be secured in place over the patient's abdomen by a connecting device 40. The connecting device 40 is depicted as a tie, but it will be understood by a person of ordinary skill in the art that alternative connecting devices such as, but not limited to hook-and-loop fasteners, buttons, or snaps may also be used.

Figure 4:
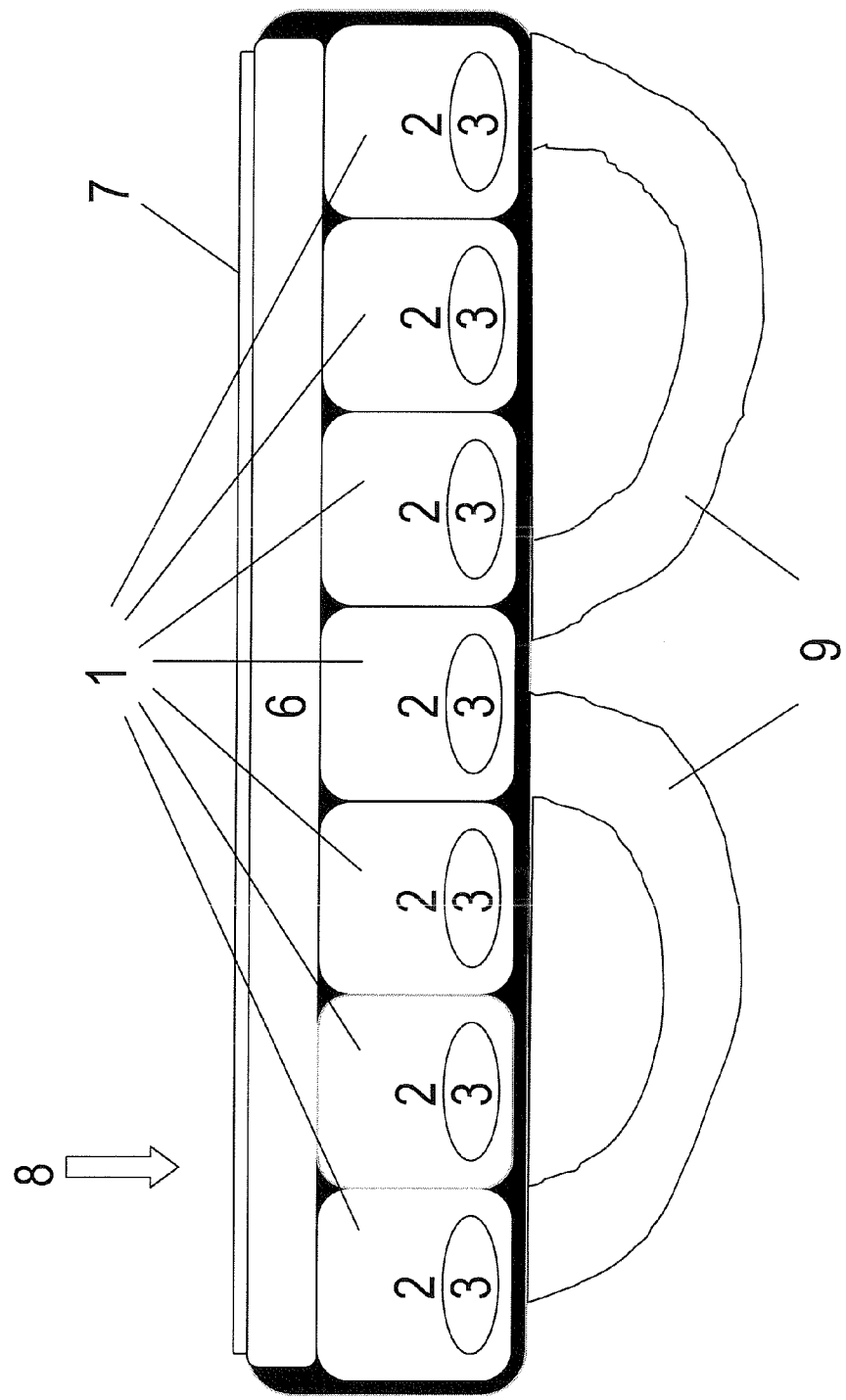
FIG. 4 is a cross-sectional view through an embodiment of an abdominal blanket.

FIG. 4 depicts an embodiment of an abdominal blanket 8. The abdominal blanket 8 of FIG. 4, further comprises at least one arm sleeve 9 which secures one or both arms and axilla against the cells 1 of the abdomen blanket 8. As shown in FIG. 4, the arm sleeves 9 are located on a side of the abdominal blanket 8 opposite a thermally conductive layer 6. Therefore, when in use, the abdominal blanket 8 is secured over the abdomen of the patient such as to place the patient's abdomen in contact with the thermally conductive layer. The patient then places his arms in the arm sleeves 9 and in contact with a back side of the cooling cells 1. In this manner, the subclavian vessels of the patient 42 are cooled. The dimensions of the abdominal blanket 8 maintain the patient's chest exposed for patient monitoring, observation, and treatment. In a further embodiment, the arm sleeve 9 includes its own cells (not depicted). Activation of one or more of the cells of the arm sleeve 9 operate in the same manner as disclosed above to provide exothermic thermal therapy directly to the arms of the patient.

Referring back to FIGS. 2 and 6, at least one groin wrap 10 extends from a lower portion 26 of the body blanket 18. The groin wrap 10 may exemplarily be two feet in length and 4-6 inches in width. The groin wrap 10 comprises cells 1 that extend the length of the groin wrap 10. The cells 1 of the groin wrap 10 operate in the same manner as described above with respect to the rest of the blanket 36. The groin wrap 10 is designed to wrap around the groin and thigh of the patient 42 to provide cooling to the femoral arteries.

A neck wrap 11 and a head wrap 12 are connected to an upper portion 24 of the body blanket 18. The neck wrap 11 and the head wrap 12 may each be approximately two feet in length and four to six inches in width. Similar in construction to the groin wrap 10, the neck wrap 11 and the head wrap 12 comprise cells 1. The neck wrap 11 and the head wrap 12 are located around the respective head and neck of the patient when the patient is positioned on the body blanket 18. The neck wrap 11 and the head wrap 12 provide thermal therapy to the brain and head blood vessels.

Referring to FIGS. 1, 2, 5, and 6, in embodiments of the thermal regulation blanket the temperature can be monitored and controlled. In one embodiment, temperature monitoring is accomplished by incorporating temperature sensitive labels 7 that comprise thermochromic ink. The temperature sensitive labels 7 are disposed above the thermally conductive layer 6. These labels 7 are designed to change color at predetermined temperatures, for example, at 42, 39, 36, 33, 30, and 27 degrees C. This may be accomplished by a single label 7 treated with different thermochromatic compounds, or may be accomplished by label groups 43 that comprise a series of labels 7 each designed to indicate a specific temperature threshold. The labels 7 and label groups 43 may also be covered with a thin layer of plastic (not depicted) which would be in contact with the patient 42 when the blanket 36 is in use and provide additional protection, durability, and a moisture barrier to the labels 7 and label groups 43.

Figure 5:
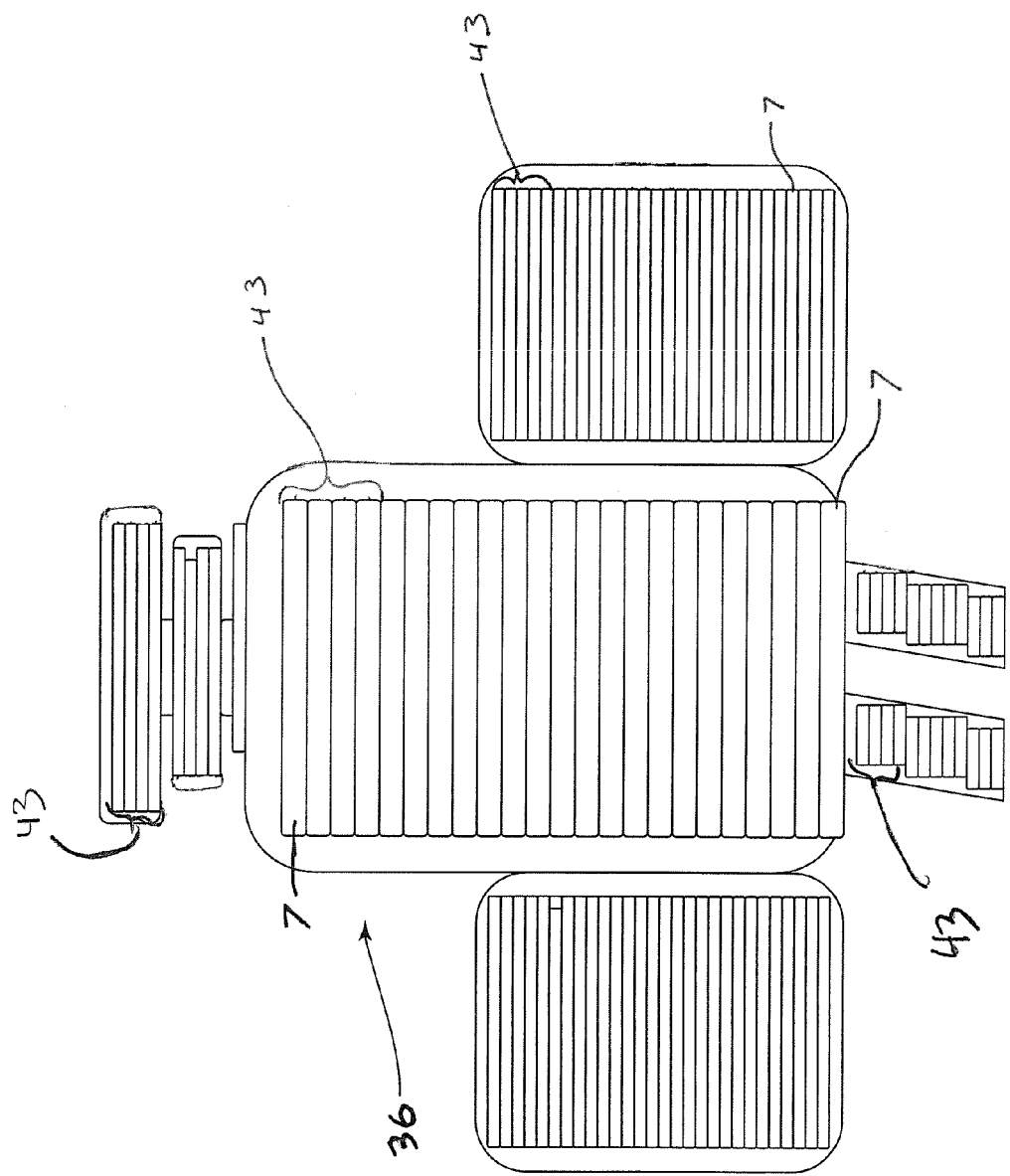
FIG. 5 depicts an embodiment of a thermal regulation blanket with temperature sensitive labels.

Referring to FIG. 5, label groups 43, including a plurality of labels with different temperature sensitivities, are placed continuously around the blanket 36. Alternatively, individual labels 7 can be arranged in a similar manner around the blanket 36. In a still further embodiment, labels 7 or label groups 43 are only located at one or more specific locations on the blanket 36. The labels are located and of a size and construction such that they will be easily seen by individuals. As noted above, the labels change color to indicate the localized temperature of the insulating layer 6 at various locations of the blanket 36, some of which may be in contact with the patient 42. A clinician can use the temperature indications of the labels to judge whether the temperature of the blanket 36 or a portion of the blanket 36, at a blanket/patient interface 44 is appropriate or inappropriate during the course of patient treatment. After an initial activation of one or more cells, subsequent cells can be later activated to maintain or adjust the temperature of the insulating layer 6 at the blanket/patient interface 44 within an appropriate range. The color of the labels at the blanket/patient interface 44 can provide the clinician with an approximation of a localized skin temperature of the patient 42.

Cells 1 can be activated sequentially to titrate the temperature of the insulating layer 6 that is exposed to the patient. Additionally, the sequential activation of the cells 1 provides new endothermic sources once the reaction in adjacent cells 1 are no longer producing an appropriate cooling temperature. In still further embodiments, the cells and pouches within the cells may comprise varying concentrations of the respective reagents or other additives. In this manner, the comparative strength, weakness, or duration of the endothermic reaction within different cells can be controlled by design. Cell shapes, positions, or labels (not depicted) can indicate to a clinician the composition of the reagents within the cell. Thus, treatment strategies can be developed to maximize the control of the thermal therapy provided to the patient. In one such strategy, the patient is quickly brought down to a target temperature, by activation of cells of a first reagent concentration, and then a maintenance phase is performed using cells with a different reagent concentration designed for temperature maintenance.

In alternative embodiments, as depicted in FIG. 5, the abdominal blanket 8, groin wrap 10, neck wrap 11, and head wrap 12 may also comprise temperature sensitive labels, such that a clinician can monitor the effective temperatures of these structures as well.

In an alternative embodiment, the temperature of the insulating layer 6 could be determined using electronic temperature sensors (not depicted) or thermometers (not depicted). The actual temperature of the mammal can be determined using ordinary means such as with by an auditory, rectal, or oral thermometer.

FIG. 7 is a flow chart that depicts an embodiment of a method 100 of providing thermal therapy to a patient. The method 100 starts at 102 when a patient is positioned on a thermal regulation blanket. The embodiments of the thermal regulation blanket include a plurality of cells filled with a first reagent. Each of the plurality of cells further include a pouch filled with a second reagent. When the first reagent and the second reagent are mixed, a thermal reaction is initiated. The thermal reaction from the mixture of the first reagent and the second reagent may be an endothermic reaction or an exothermic reaction depending on the reagents selected. In an embodiment of the thermal regulation blanket, a thermally conductive layer is disposed over one or more of the cells. The thermally conductive layer distributes the cold from the endothermic reaction or the heat from the exothermic reaction.

In an embodiment, the patient is positioned such as to engage a back and a buttocks of the patient with a body blanket component of the thermal regulation blanket. Dividers located in the body blanket in between the cells of the plurality of cells provide support to the patient while the patient engages the body blanket. The dividers further prevent the weight of the patient from collapsing the cells or prematurely rupturing any pouches.

At 104, an abdomen of the patient is engaged by an abdominal blanket component of the thermal regulation blanket. In an alternative embodiment the abdomen of the patient is engaged by two or more abdominal blankets of the thermal regulation blanket. Each abdominal blanket includes one or more cells as described above. The abdominal blanket secures over the abdomen of the patient. In an embodiment, the abdominal blanket is dimensioned such that a chest of the patient remains exposed even after the abdominal blanket is secured over the abdomen of the patient.

In an alternative embodiment, the abdominal blanket further includes at least one arm sleeve on a side of the abdominal blanket opposite the side of the abdominal blanket that engages the abdomen of the patient. At least one arm of the patient is placed within the at least one arm sleeve. The arm sleeve secures the arm of the patient in engagement with the one or more cells of the abdominal blanket. The engagement of the arm with the one or more cells of the abdominal blanket directs thermal therapy to a subclavian vessel of the patient when at least one of the one or more cells of the abdominal blanket are activated.

At least one cell of the thermal regulation blanket is activated at 106. To activate at least one cell, the first reagent and the second reagent in the cell are allowed to mix. This mixture can be initiated in a variety of ways, including with the rupture of the pouch that is filled with the second reagent. The mixture of the first reagent and the second reagent causes a thermal reaction to take place within the cell. This thermal reaction either adds additional heat to the system or removes heat from the system. The activation of at least one cell starts the provision of thermal therapy to the patient. Effective thermal therapy may include the activation of a plurality of cells of the thermal regulation blanket, including one or more cell of the body blanket and one or more cell of the abdominal blanket.

After the thermal therapy is started at 106, a temperature of at least one location of the thermal therapy provided by the thermal regulation blanket is monitored at 108. In one embodiment, the temperature of the at least one location of the thermal therapy can be monitored by visually observing a color change of a label treated with thermochromatic ink. One or more of such thermochromatically treated labels are adhered to locations on the thermal regulation blanket.

In an alternative embodiment, the thermochromatic labels are affixed to the thermal regulation blanket at a blanket/patient interface. A change in color of these thermochromatic labels is therefore representative of a localized temperature at the interface between the blanket and the patient.

After monitoring the temperature of at least one location of the thermal therapy, at least one additional cell is activated at 110 to adjust the temperature of the at least one location. Exemplarily, visual inspection of one or more thermochromatic labels may indicate that a localized region of a patient receiving hypothermic therapy is warming above a desired temperature. In response to this indication, additional endothermic cells can be activated in the localized area can be activated to decrease the temperature.

It will be recognized from the present disclosure that alternative embodiments of the method as described herein include additional features and functionalities of the embodiments of the thermal regulation blanket apparatus disclosed above. A person of ordinary skill will recognize that the features and functionalities of these apparatus embodiments can be incorporated into embodiments of the method without undue experimentation.

The embodiments of the apparatus and methods disclosed herein have primarily used the example of an adult human patient. It is to be understood that similar embodiments are applicable to children and infants, particularly if such embodiments of the thermal regulation blanket are dimensioned for such patients. Also, it is considered within the scope of the present disclosure that embodiments may be similarly applicable to the veterinary field for the treatment of any mammal.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A thermal regulation blanket for providing thermal therapy to a patient, the thermal regulation blanket comprising:
   a body blanket constructed of a first plurality of cells, each of the cells of the plurality of cells separated by a plurality of dividers, each of the cells of the first plurality includes a first reagent, a first plurality of pouches are each disposed within a respective cell of the first plurality of cells and each pouch of the first plurality of pouches include a second reagent, and a first thermally conductive layer disposed over the first plurality of cells and the plurality of dividers, such that the thermally conductive layer creates a thermal interface between the patient and the first plurality of cells; and
   at least one abdominal blanket attached to the body blanket, the at least one abdominal blanket is constructed of a second plurality of cells that each include the first reagent, a second plurality of pouches each include the second reagent, each of the second plurality of pouches are disposed within a respective cell of the second plurality of cells, and a second thermally conductive layer disposed over the second plurality of cells;
   wherein the at least one abdominal blanket is dimensioned to cover a substantially smaller portion of the patient's torso than the body blanket and is attached to the body blanket, such that when the body blanket is aligned with the posterior surface of the patient the at least one abdominal blanket may be aligned with a portion of the anterior surface of the patient's torso below the shoulders; and
      wherein rupture of any pouch of the first or second plurality of pouches causes the second reagent to mix with the first reagent within the respective cell, and when the first reagent and the second reagent mix, thermal reaction occurs that modifies the temperature of a respective thermally conductive layer.

2. The thermal regulation blanket of claim 1, further comprising at least one groin wrap that extends away from a lower portion of the body blanket.

3. The thermal regulation blanket of claim 1, further comprising a neck wrap that extends away from an upper portion of the body blanket.

4. The thermal regulation blanket of claim 3, further comprising a head wrap that extends away from the neck wrap in a direction opposite the body blanket.

5. The thermal regulation blanket of claim 1, wherein the at least one abdominal blanket further comprises at least one arm sleeve on a side of the abdominal blanket opposite the second thermally conductive layer, the at least one arm sleeve comprises a third plurality
   of cells filled with the first reagent, and a third plurality of pouches filled with the second reagent, each of the pouches disposed within a respective cell of the third plurality of cells.

6. The thermal regulation blanket of claim 1, wherein the at least one abdominal blanket comprises two abdominal blankets, and each abdominal blanket is releasably secured to an opposite side of the body blanket.

7. The thermal regulation blanket of claim 6, wherein each of the abdominal blankets comprises an arm sleeve on the a side of the abdominal blanket opposite the second thermally conductive layer.

8. A method of providing thermal therapy to a patient, the method comprising:
   positioning the patient on a thermal regulation blanket, the thermal regulation blanket comprising a body blanket and at least one abdominal blanket, the body blanket comprised of a plurality of cells;
   engaging an abdomen of the patient with at least one abdominal blanket of the thermal regulation blanket, the at least one abdominal blanket comprising at least one cell filled with a first reagent with a pouch disposed within the cell filled with a second reagent;
   activating at least one cell of each of the plurality of cells of the body blanket and the at least one cell of the abdominal blanket by mixing the first reagent and the second reagent in at least one cell of each to begin providing thermal therapy to the patient;
   monitoring a temperature of at least one location of the thermal regulation blanket with a temperature sensor; and
   activating at least one additional cell to adjust the temperature of the thermal regulation blanket at the at least one location.

9. The method of claim 8, wherein positioning the patient on the thermal regulation blanket further comprises engaging a back and buttocks of the patient with a body blanket of the thermal regulation blanket.

10. The method of claim 8, further comprising:
    placing at least one arm of the patient within a sleeve formed in the abdominal blanket, the sleeve formed in the abdominal blanket holds the at least one rum in engagement with the at least one cell of the abdominal blanket; and
    activating the at least one cell of the abdominal blanket to provide thermal therapy to a subclavian vessel of the patient.

11. The method of claim 8, further comprising monitoring the temperature of at least location that is at a blanket/patient interface with a thermochromatic sensor disposed between the thermal regulation blanket and the patient.

12. The method of claim 8 wherein the patient is positioned with his posterior portion facing the body blanket and his the abdomen is engaged by the abdominal blanket such that a significant portion of the anterior portion of the patient between his arms and his abdomen is exposed.

13. A thermal regulation blanket for providing thermal therapy to a patient, the thermal regulation blanket comprising:
   a body blanket constructed of a first plurality of cells, each of the cells of the plurality of cells separated by a plurality of dividers, each of the cells of the first plurality includes a first reagent disposed in a first portion of the cell, a second reagent disposed in a second portion of the cell and a rupturable plastic partition separating the two portions and rupturing upon the application of a predetermined amount of pressure which is less than that which would cause a rupture of the cell, and a first thermally conductive layer disposed over the first plurality of cells and the plurality of dividers, such that the thermally conductive layer creates a thermal interface between the patient and the first plurality of cells; and at least one abdominal blanket attached to the body blanket, the at least one abdominal blanket is constructed of a second plurality of cells that each includes the first reagent disposed in a first portion of the cell, the second reagent disposed in a second portion of the cell and a rupturable plastic partition separating the two portions and rupturing upon the application of a predetermined amount of pressure which is less than that which would cause a rupture of the cell, and a second thermally conductive layer disposed over the second plurality of cells;

wherein the at least one abdominal blanket is dimensioned to cover a substantially smaller portion of the patient's torso than the body blanket and is attached to the body blanket such that when the body blanket is aligned with the posterior surface of the patient the at least one abdominal blanket may be aligned with a portion of the anterior surface of the patient's torso below the shoulders; and wherein rupture of any plastic partition of the first or second plurality of cells causes the second reagent to mix with the first reagent within the respective cell, and when the first reagent and the second reagent mix, thermal reaction occurs that modifies the temperature of a respective thermally conductive layer.

14. The thermal regulation blanket of claim 13 wherein the second plurality of cells of the abdominal blanket have a tubular configuration with a long axis both substantially longer than the short axis and parallel to the line of juncture between the abdominal blanket and the body blanket.

\* \* \* \* \*